US00PP30721P2

(12) United States Plant Patent
Flore

(10) Patent No.: US PP30,721 P2
(45) Date of Patent: Jul. 16, 2019

(54) ***PHALAENOPSIS* PLANT NAMED 'MI00708'**

(50) Latin Name: *Phalaenopsis hybrida*
Varietal Denomination: MI00708

(71) Applicant: Febe Flore, Lochristi (BE)

(72) Inventor: Febe Flore, Lochristi (BE)

(73) Assignee: Floreac N.V. div. Microflor, Lochristi (BE)

( * ) Notice: Subject to any disclaimer, the term of this patent is extended or adjusted under 35 U.S.C. 154(b) by 0 days.

(21) Appl. No.: 15/732,946

(22) Filed: Jan. 12, 2018

(51) Int. Cl.
*A01H 6/62* (2018.01)
*A01H 5/02* (2018.01)

(52) U.S. Cl.
USPC ..... Plt./311

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Phalaenopsis* plant named 'MI00708', characterized by its upright plant habit; moderately vigorous growth habit; strong flowering stems; and freely flowering habit with typically three racemes per plant with each inflorescence with numerous yellow-colored flowers.

2 Drawing Sheets

Botanical designation: *Phalaenopsis hybrida.*
Cultivar denomination: 'MI00708'.

BACKGROUND OF THE INVENTION

The present invention relates to a new and distinct cultivar of *Phalaenopsis* plant, botanically known as *Phalaenopsis hybrida*, and hereinafter referred to by the name 'MI00708'.

The new *Phalaenopsis* plant is a product of a planned breeding program conducted by the Inventor in Lochristi, Belgium. The objective of the breeding program is to develop new freely flowering *Phalaenopsis* plants with good leaf shape and unique and attractive flower patterns and coloration.

The new *Phalaenopsis* plant originated from a cross-pollination in August, 2009 in Lochristi, Belgium of a proprietary selection of *Phalaenopsis hybrida* identified as code number PH01654, not patented, as the female, or seed, parent with a proprietary selection of *Phalaenopsis hybrida* identified as code number PH00891, not patented, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in June, 2012.

Asexual reproduction of the new *Phalaenopsis* plant by in vitro meristem propagation in a controlled environment in Lochristi, Belgium since April, 2014 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'M100708'. These characteristics in combination distinguish 'MI00708' as a new and distinct *Phalaenopsis* plant:

1. Upright plant habit.
2. Moderately vigorous growth habit.
3. Strong flowering stems.
4. Freely flowering habit with typically three racemes per plant, each inflorescence with numerous flowers.
5. Yellow-colored flowers.

Plants of the new *Phalaenopsis* can be compared to plants of the female parent selection. Plants of the new *Phalaenopsis* differ primarily from plants of the female parent selection in flower color as flowers of the female parent selection are darker yellow in color.

Plants of the new *Phalaenopsis* can be compared to plants of the male parent selection. Plants of the new *Phalaenopsis* differ primarily from plants of the male parent selection in flower color as plants of the male parent selection are white in color.

Plants of the new *Phalaenopsis* can be compared to plants of *Phalaenopsis hybrida* 'Golden Beauty', not patented. In side-by-side comparisons, plants of the new *Phalaenopsis* differ primarily from plants of 'Golden Beauty' in flower color as flowers of the new *Phalaenopsis* are lighter yellow in color. In addition, plants of the new *Phalaenopsis* have branched racemes whereas plants of 'Golden Beauty' have non-branched racemes.

Plants of the new *Phalaenopsis* can also be compared to plants of *Phalaenopsis hybrida* 'Miraflore 351709', not patented. In side-by-side comparisons, plants of the new *Phalaenopsis* differ primarily from plants of 'Miraflore 351709' in the following characteristics:

1. Plants of the new *Phalaenopsis* are faster growing than plants of 'Miraflore 351709'.

2. Plants of the new *Phalaenopsis* have narrower leaves than plants of 'Miraflore 351709'.
3. Flowers of plants of the new *Phalaenopsis* are darker yellow in color than flowers of plants of 'Miraflore 351709'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet is a side perspective view of a typical flowering plant of 'MI00708' grown in a container.

The photograph on the second sheet is a close-up view of a typical flower of 'MI00708'.

DETAILED BOTANICAL DESCRIPTION

The aforementioned photographs and following observations and measurements describe plants grown during the autumn and early winter in 10-cm containers in a glass-covered greenhouse in Lochristi, Belgium and under cultural practices typically used in commercial *Phalaenopsis* production. During the production of the plants, day and night temperatures ranged from 18° C. to 29° C. and light levels ranged from 150 Watt/m$^2$ to 375 Watt/m$^2$. Plants were 76 weeks old when the photographs and description were taken. In the following description, color references are made to The Royal Horticultural Society Colour Chart, 2015 Edition, except where general terms of ordinary dictionary significance are used.

Botanical classification: *Phalaenopsis hybrida* 'MI00708'.

Parentage:

*Female parent*.—Proprietary selection of *Phalaenopsis hybrida* identified as code number PH01654, not patented.

*Male parent*.—Proprietary selection of *Phalaenopsis hybrida* identified as code number PH00891, not patented.

Propagation:

*Type*.—By in vitro meristem propagation.

*Time to initiate roots, summer*.—About nine to ten weeks at temperatures about 26° C.

*Time to initiate roots, winter*.—About ten to eleven weeks at temperatures about 26° C.

*Time to produce a rooted young plant, summer*.—About 140 to 160 days at temperatures about 26° C.

*Time to produce a rooted young plant, winter*.—About 150 to 180 days at temperatures about 26° C.

*Root description*.—Thick, fleshy; typically grey green in color, towards the apex, close to light green; actual color of the roots is dependent on substrate composition, water quality, fertilizer, substrate temperature and age of roots.

*Rooting habit*.—Low to non-branching; sparse.

Plant description:

*Plant form and growth habit*.—Herbaceous epiphyte; upright plant habit with typically three branched racemes per plant, each inflorescence with numerous flowers; monopodial; moderately vigorous growth habit and moderate growth rate.

*Plant height, substrate level to top of foliar plane*.—About 13.3 cm.

*Plant height, substrate level to top of inflorescences*.—About 51.8 cm.

*Plant diameter or spread*.—About 28.3 cm.

Leaf description:

*Arrangement and quantity*.—Distichous, simple; sessile; about six per plant.

*Length*.—About 17.7 cm.

*Width*.—About 6.1 cm.

*Aspect*.—Mostly flat.

*Shape*.—Narrowly elliptical; slightly carinate.

*Apex*.—Broadly acute, unequal.

*Base*.—Sheathing.

*Margin*.—Entire; slightly revolute.

*Texture and luster, upper and lower surfaces*.—Slightly furrowed, glabrous; slightly glossy.

*Venation pattern*.—Camptodromous.

*Color*.—Developing leaves, upper surface: Close to NN137B. Developing leaves, lower surface: Close to 147B strongly tinged with close to N186C. Fully expanded leaves, upper surface: Close to NN137A to NN137B; venation, close to NN137A. Fully expanded leaves, lower surface: Close to between 146B and 147B; towards the margins, slightly tinged with close to N199B; venation, close to between 146B and 147B.

Inflorescence description:

*Appearance and flowering habit*.—Showy zygomorphic flowers arranged on axillary branched racemes; typically three racemes per plant; each inflorescence with about 14 flowers; flowers face outwardly to slightly nodding on arching inflorescences supported by upright peduncles; flowers with three petals, two lateral petals and one center petal transformed into a labellum and three sepals.

*Fragrance*.—None detected.

*Time to flower*.—Plants begin flowering about 18 weeks after an inductive cooling period.

*Flower longevity*.—Long flowering period, individual flowers maintain good substance for about two months on the plant; flowers not persistent.

*Inflorescence length* (*lowermost flower to inflorescence apex*).—About 21.4 cm.

*Inflorescence width*.—About 14.2 cm.

*Flower buds*.—Height: About 1.9 cm. Diameter: About 1.2 cm. Shape: Broadly ovate. Color: Close to between N144A and 151B; towards the apex, close to 174B.

*Flower diameter*.—About 7 cm by 8.4 cm.

*Flower depth*.—About 3.2 cm.

*Petals, quantity and arrangement*.—Three, two lateral petals and one center petal transformed into a labellum.

*Lateral petals*.—Length: About 4 cm. Width: About 5.1 cm. Shape: Reniform. Apex: Rounded. Margin: Entire. Texture and luster, upper and lower surfaces: Smooth, glabrous, velvety; matte. Color: When opening, upper surface: Close to 4B to 4C; towards the margins, close to between 4D and 5D; at the base, close to 70C to 70D; faint venation, close to 51B. When opening, lower surface: Close to 4C; towards the margins, close to between 4D and 5D; faint venation, close to 51B. Fully opened, upper surface: Close to 4C to 4D; towards the base, close to 4D; at the base, close to 70C to 70D; faint venation, close to 70C. Fully opened, lower surface: Close to between 4D and 155A; faint venation, close to 70D.

*Labellum*.—Appearance: Tri-lobed with two lateral lobes and a central lobe. Length, lateral lobe: About 2.2 cm. Width, lateral lobes: About 1.6 cm. Length, central lobe: About 2.3 cm. Width, central lobe: About 2 cm. Shape, lateral lobes: Obovate. Shape, central lobe: Roughly rhomboidal to deltoid. Apex, lateral lobes: Obtuse. Apex, central lobe: Cleft with two moderately long narrow recurved cirrose tips. Margins, lateral lobes: Entire, undulate. Margins, central lobe: Entire. Texture and luster, upper and lower surfaces: Smooth, glabrous, velvety; matte. Callosities: Located at the base of the labellum and attachment point of the lateral petals; about 4.5 mm in length, about 6 mm in width and about 4 mm in height. Color: When opening and fully opened, upper surface: Lateral lobes: Close to 64C to 64D; towards the base, close to 155A; basal margins, close to 167A; venation, close to 180A. Central lobe: Close to between 61B and 63A; towards the margins, close to 167B; at the base, close to 6C; cirrose apices, close to 14C. Callosities: Close to between 12A and 13A; finely dotted, close to 183B. When opening and fully opened, lower surface: Lateral lobes: Close to 180A; towards the apex and the base, close to 155C. Central lobe: Close to 22B; center and towards the margins, close to 64C; central band and at the base, close to 155A and 155C; cirrose apices, close to 65B.

*Sepals*.—Quantity and arrangement: Three, two lower lateral sepals and one upper dorsal sepal. Length, lateral sepal: About 4.1 cm. Width, lateral sepals: About 2.5 cm. Length, dorsal sepal: About 4.2 cm. Width, dorsal sepal: About 2.8 cm. Shape, lateral and dorsal sepals: Ovate. Apex, lateral sepals: Bluntly acute. Apex, dorsal sepal: Obtuse to bluntly acute. Base, lateral and dorsal sepals: Truncate. Margin, lateral and dorsal sepals: Entire. Texture and luster, lateral and dorsal sepals, upper and lower surfaces: Smooth, glabrous, velvety; matte. Color, lateral sepals: When opening, upper surface: Close to between 3C and 4C; towards the base, finely dotted and venation, close to 61A. When opening, lower surface: Close to 5C; faint venation, close to N170B. Fully opened, upper surface: Close to 2C; towards the margins, 4D; towards the base, finely dotted and venation, close to 61A. Fully opened, lower surface: Close to between 4C and 5D; towards the base, close to 4D; faint venation, close to 180C. Color, dorsal sepal: When opening, upper surface: Close to between 3C and 4C slightly tinged and veined with close to 61D. When opening, lower surface: Close to 5C. Fully opened, upper surface: Close to 2C; towards the margins, close to 4D; slightly tinged with close to 61C and 61D. Fully opened, lower surface: Close to between 4C and 5D; towards the base, close to 4D.

*Peduncles*.—Length: About 60.1 cm. Diameter: About 5 mm. Strength: Very strong. Aspect: Upright to about 40° from vertical. Texture and luster: Smooth, glabrous; matte. Color: Close to 200B with fine dots, close to 147D.

*Pedicels*.—Length: About 3.7 cm. Diameter: About 3 mm. Strength: Moderately strong. Aspect: About 65° from peduncle axis. Texture and luster: Smooth, glabrous; matte. Color: Close to N148D; distally, tinged with close to 70C to 70D; proximally, tinged with close to 152D.

*Reproductive organs*.—Androecium: Column length: About 7 mm. Column width: About 5 mm. Column color: Close to NN155B. Pollinia quantity: Two. Pollinia diameter (per two pollinia): About 2 mm. Pollinia color: Close to 23A. Gynoecium: Stigma length: About 3 mm. Stigma width: About 4 mm. Stigma shape: Reniform. Stigma color: Close to 157C. Ovary length: About 3 mm. Ovary diameter: About 1.5 mm. Ovary color: Close to lighter than 145D. Seeds and fruits: Seed and fruit development have not been observed on plants of the new *Phalaenopsis* to date.

Pathogen & pest resistance: Plants of the new *Phalaenopsis* have not been shown to be resistant to pathogens and pests common to *Phalaenopsis* plants.

Temperature tolerance: Plants of the new *Phalaenopsis* have been observed to tolerate high temperatures of about 40° C. and suitable for USDA Hardiness Zone 10.

It is claimed:

1. A new and distinct *Phalaenopsis* plant named 'MI00708' as illustrated and described.

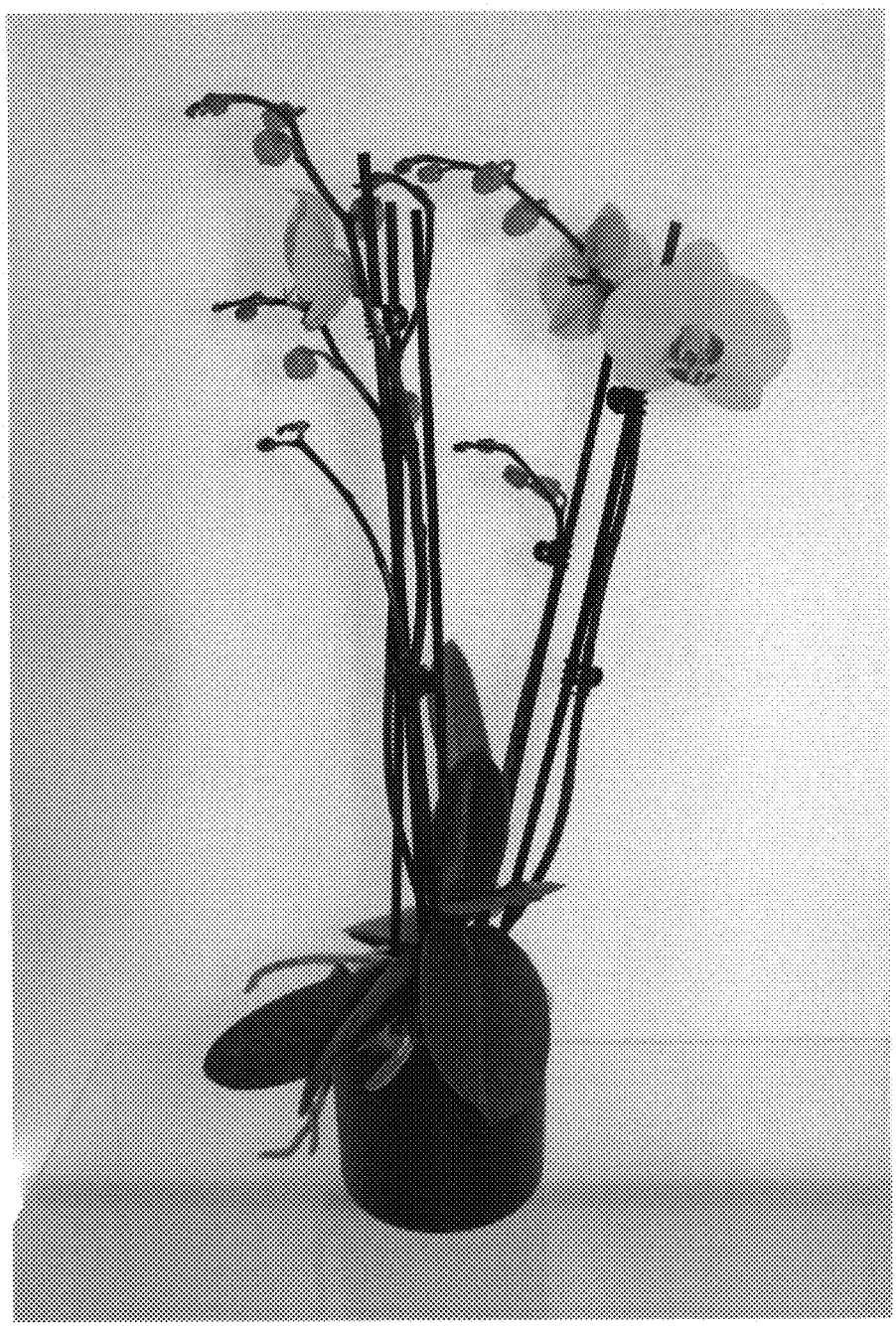

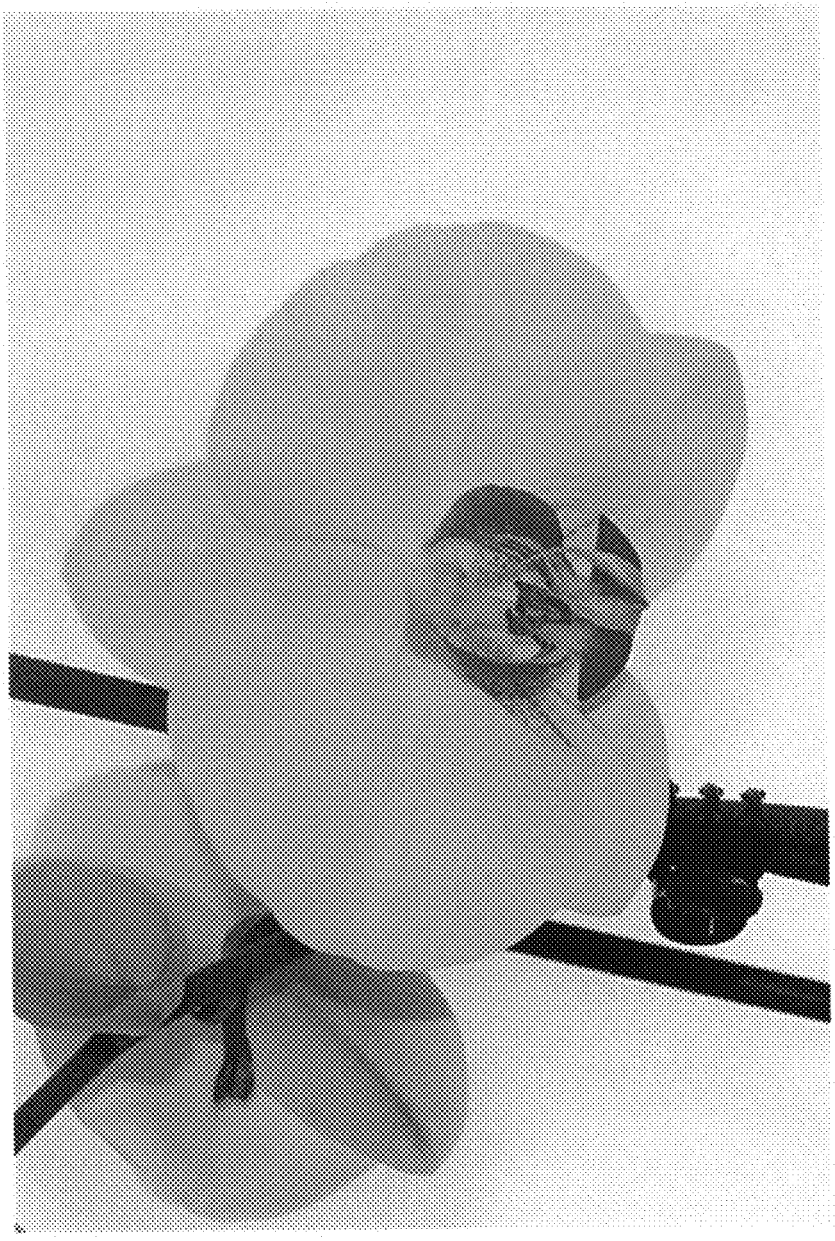

* * * * *